United States Patent [19]

Iadipaolo et al.

[11] Patent Number: 4,759,074
[45] Date of Patent: Jul. 19, 1988

[54] METHOD FOR AUTOMATICALLY INSPECTING PARTS UTILIZING MACHINE VISION AND SYSTEM UTILIZING SAME

[75] Inventors: Rene M. Iadipaolo, Southfield; Jeanne T. Merchant, Royal Oak; Kurt A. Tesnow, Warren, all of Mich.

[73] Assignee: General Motors Corporation, Detroit, Mich.

[21] Appl. No.: 925,361

[22] Filed: Oct. 28, 1986

[51] Int. Cl.[4] .............................................. G06K 9/46
[52] U.S. Cl. .......................................... 382/23; 382/8
[58] Field of Search ................ 382/8, 24, 23; 358/106

[56] References Cited

U.S. PATENT DOCUMENTS

| | | | |
|---|---|---|---|
| 4,296,405 | 10/1981 | Rich | 382/8 |
| 4,376,951 | 3/1983 | Miyazawa | 358/106 |
| 4,454,542 | 6/1984 | Miyazawa | 358/106 |
| 4,486,775 | 12/1984 | Catlow | 358/106 |
| 4,521,807 | 6/1985 | Werson | 382/8 |
| 4,581,632 | 4/1986 | Davis et al. | 358/106 |
| 4,581,762 | 4/1986 | Lapidus et al. | 382/8 |
| 4,644,583 | 2/1987 | Watanabe et al. | 382/22 |

*Primary Examiner*—Leo H. Boudreau
*Attorney, Agent, or Firm*—Albert F. Duke

[57] ABSTRACT

A method for automatically inspecting parts utilizing machine vision and system utilizing same are disclosed wherein a large variety of parts are inspected with a single optical setup at a vision station. Cameras and their respective illuminating lamps are located at the vision station. The inspection task requires multiple scenes or views to inspect part features such as inner and outer diameters, part height and concentricity. Initially, the system is taught which features of the parts are to be inspected by generating reference data. The reference data includes predetermined feature-detecting algorithms, model data defining typical features and limit data which is related to the allowable deviation of the features. The parts to be inspected are conveyed past the vision station. The signals from each of the active cameras are digitized and then processed by its own group of pipelined processors. Each group of processors is programmed with the reference data to process the gray-scale digitized data to determine whether the features appearing in a particular view of the part are acceptable. A coordination processor coordinates the operation of the groups of processors and is responsive to the transport signal. A general purpose computer is responsive to the part sense signals and feature-acceptance signals from each of the groups of processors to provide reject signals for use by an actuator to remove unacceptable parts from the path of conveyance.

11 Claims, 11 Drawing Sheets

| DATA TYPE | RISING CORNER | PLATEAU |
|---|---|---|
| PIXEL OFFSET | 1 | 1 |
| GREY LEVEL RANGE | | |
|   PIXEL | 0 → 0 | 50 → 63 |
|   PIXEL BEFORE | 0 → 0 | 50 → 63 |
|   PIXEL AFTER | 1 → 63 | 50 → 63 |
| OPERATION | SUBTRACT | SUBTRACT |
| RESULT 1 HIGH LIMIT | 0 | -13 |
| RESULT 1 LOW LIMIT | 0 | 13 |
| RESULT 2 HIGH LIMIT | 63 | -13 |
| RESULT 2 LOW LIMIT | 1 | 13 |

1 RISING CORNER RAY 1
2 FALLING CORNER RAY 1
3 RISING CORNER RAY 1
4 FALLING CORNER RAY 1
5 RISING CORNER RAY 2
6 FALLING CORNER RAY 2
7 RISING CORNER RAY 2
8 FALLING CORNER RAY 2

METHOD FOR AUTOMATICALLY INSPECTING PARTS UTILIZING MACHINE VISION AND SYSTEM UTILIZING SAME

TECHNICAL FIELD

This invention relates in general to part inspection methods and systems utilizing machine vision and, in particular, to part inspection methods and systems utilizing gray scale machine vision.

BACKGROUND ART

A resurgence in the part forging industry has brought about new processing techniques which produce cost-effective, near net shape forgings at high production rates. In particular, the automotive part forging industry now produces high-strength, lower weight forgings which thereby reduce the weight of the resulting vehicle. A wide variety of such automotive parts are now produced at relatively high production rates and, after they are cooled, they are inspected on a sampling basis.

Inspection techniques commonly used to inspect such parts are a combination of optical comparators, mechanical gauges and experienced inspectors who must remember the differences between acceptable and unacceptable parts. Some of the shortcomings of the present method and apparatus are as follows: (1) non-uniform and subjective inspections; (2) inability to inspect parts at production rates; (3) uncertainty in the quality of the parts being shipped; (4) lack of documentation to correct or improve the part production process; (5) not easily adaptable to the introduction of new production parts; and (6) does not allow full implementation of other "factory of future" technologies.

The potential value within the manufacturing industry for machine vision systems with the flexibility and acuity of human sight is widely recognized. Unfortunately, the development of a general purpose vision technology has not been as successful as hoped. No single technology has proven to be capable of handling a significant spectrum of applications. Most available systems function only within selected market niches and perform disappointingly elsewhere.

The objective for any vision system is to process the pixels in the image array in such a manner as to separate the object of interest from the background and the noise. Difficulty arises when a classic serial computer is applied to doing operations on such a large block of data. Most popular 16 or 32 bit micro-computers require 10 to 15 seconds to perform a simple noise reducing filter operation. This amount of processing time is totally unacceptable for most industrial tasks. As a result, a major objective of those who have sought to deal with industrial vision problems has been to reduce or simplify the image data.

Full gray scale processing systems hold the promise of an acceptable approach to solving industrial vision problems. In recent years hardware began to emerge that made it possible to cost-effectively process gray scale data in times that are acceptable for industrial problem solving.

An example of this type of architecture makes extensive use of pipelined hardware. In this approach the successive steps for processing each element of data are implemented in a separate piece of hardware. If the process requires eight successive operations to complete, then the pipe is constructed of eight successive stages of processing. The first data element entering the processor completes the first stage of processing and enters the second stage as the second element is clocked into the first stage. This process continues until each stage of the pipeline is working on a different element of the data stream. The first element of data processed emerges from the end of the pipe in the normal processing time. The second element of data emerges $\frac{1}{8}$ of the time later and so on until the data stream is exhausted.

Inspection of parts at production rates by machine vision has been implemented in some isolated cases where either a general purpose system could be adapted to a particular application or a special system has been devised to take advantage of some peculiarity of the parts or the inspection requirements. In each case the systems are limited such that applications needing real time processing of massive amounts of visual data would be prohibitively large and expensive. Often the prior systems could not be upgraded to high capacity without loss of speed. In other cases the systems are inflexible; that is, the systems do not readily accommodate a large variety of different part geometries or do not easily accept new part configurations.

SUMMARY OF THE INVENTION

An object of the present invention is to provide an improved method and system utilizing machine vision to automatically inspect a part in a quick and accurate fashion by identifying and locating at least one specific feature of the part, such as an outer boundary, and by comparing the feature with a corresponding taught feature.

Another object of the present invention is to provide an improved method and system utilizing machine vision for automatically inspecting a part from located features of different scenes of the part wherein the located features are subsequently compared to allowable taught deviations of such features.

Still another object of the present invention is to provide a method and system utilizing machine vision for automatically inspecting a wide variety of parts with a single optical setup at a vision station wherein the parts are inspected in a quantitative and uniform fashion.

Yet still another object of the present invention is to provide a method and system utilizing machine vision for automatically inspecting a wide variety of parts without substantially changing the method and/or system wherein groups of coordinated pipelined processors process gray-scale data representing different scenes of the same part.

In carrying out the above objects and other objects of the present invention, a method is provided for automatically inspecting a part at a vision station comprising the steps of: generating a gray-scale digital image of the part to be inspected; detecting feature points corresponding to at least one feature of the part by scanning along a pattern of lines in the image, each line comprising a series of gray-scale pixels, and comparing sequences of pixels in the line to a criteria for each feature of interest to determine feature point coordinates; storing sets of detected feature point coordinates in separate tables for each feature; and comparing each set of feature points to a predetermined reference set of feature points to determine whether the part is acceptable.

Preferably, the method is utilized to automatically inspect a plurality of substantially identical parts. When utilized in this fashion, the parts are conveyed from an upstream position to a downstream position and a transport signal corresponding to the distance that the parts are conveyed along the path of conveyance is generated. The parts are sensed as they are conveyed from the upstream position to the downstream position to provide part sense signals. Also, gray-scale digital images are generated, each of which contains a different view of the part to be inspected. For each image at least one predetermined feature-detecting algorithm is performed and the located feature data is compared with the allowable deviation for each respective feature. The transport, part sense and feature acceptance signals are processed to provide a reject signal for use by an actuator to remove unacceptable parts from the path of conveyance.

Further in carrying out the above objects and other objects of the present invention, a system is provided for carrying out each of the above steps. The system comprises means for generating a gray-scale digital image containing the part to be located at the vision station, said means for generating including at least one television camera; means for storing tables containing feature reference data relating to at least one feature of an ideal part, a predetermined data type detecting algorithm for each type of feature to locate data type sets within the digital image and limit data relating to the allowable deviation of the feature; means for performing the algorithm with at least a portion of the digital image to provide data type sets; means for sorting the data type sets into separate features and storing the feature data in separate tables, and means for comparing the located feature data with the reference data to determine whether the part is acceptable.

The advantages of the above-described method and system are numerous. For example, such gray-scale vision processing is fast enough to provide 100% inspection of parts in a quantitative and uniform fashion. Also, the method and system are flexible enough to inspect a wide variety of parts at high production rates by merely having an operator teach the system certain operating parameters of the system. Finally, the method and system are capable of providing information that can be used to correct or improve the production process of the parts and is compatible with other "factory of the future" technologies.

Other advantages of the present invention will be readily appreciated as the same becomes better understood with reference to the following detailed description when considered in connection with the accompanying drawings.

BEST MODE FOR CARRYING OUT THE INVENTION

Figure 1:
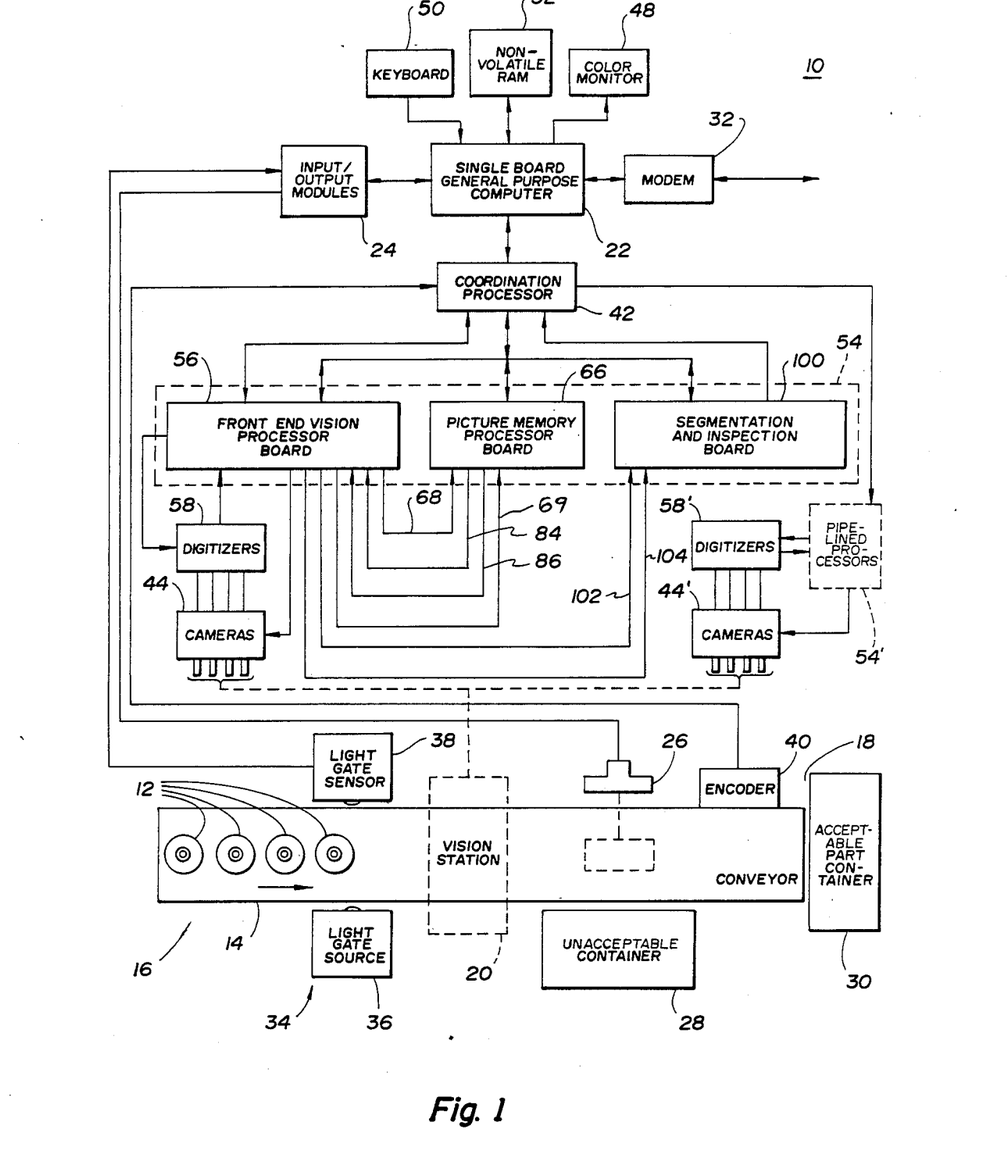
FIG. 1 is a schematic view, illustrating the method and system of the present invention with respect to parts, such as automotive parts.

Referring to FIG. 1 there is illustrated a system collectively indicated by reference numeral 10 for automatically inspecting a plurality of parts at production rates by utilizing machine vision.

In the particular embodiment of the present invention, the parts to be inspected comprise forged automotive parts 12 which, typically, can be classified into six families of such parts such as speed gears, side gears, spindles and sleeves. The parts 12 are initially produced by hot formers at the rate of approximately 80 to 100 pieces per minute. The forgings are then loaded onto an automated guided vehicle system for material handling and are subsequently loaded by material loading equipment onto a moving conveyor 14 of the system 10 for conveyance of the parts 12 from an upstream position 16 to a downstream position 18.

In general, the conveyor 14 conveys the parts 12 through a vision station 20 located along the path of conveyance for inspection of the parts 12. Typical features of the parts 12 to be inspected include inner and outer diameters, part height, flange height, no fill and concentricity. In the particular embodiment of the present invention a maximum of six scenes or views per part may be analyzed with a maximum of 11 geometric features per scene.

The final accept/reject decision for each part based on machine vision inspection is made by a general purpose computer 22. The action taken after the final decision is made may vary from application to application. However, as illustrated in the preferred embodiment of the present invention, when the inspection process reveals an "unacceptable part", the general purpose computer 22 provides a signal to input/output modules 24 which, in turn, provide a signal to activate a reject actuator 26 or pneumatic kicker which kicks the rejected part off the conveyor 14 and into a "unacceptable" part container 28. Accepted parts continue to be conveyed on the conveyor 14 until conveyed into an acceptable part container 30 which, in turn, is shipped either to another part of the plant for further processing or to a different plant.

The general purpose computer 22 also is coupled to a modem 32 to allow the computer 22 to communicate externally with other devices such as programmable controllers, numerically controlled machinery, other vision systems, plant data management systems and the like. Preferably, the computer 22 communicates with a plant communication system to provide dimensional trends for tooling control based upon statistics generated as to the number of acceptable and rejected parts.

As the parts 12 are conveyed by the conveyor 14, they are sensed by a sensor means or mechanism, generally indicated at 34, located along the path of conveyance. The sensor mechanism 34 provides part sense signals upon sensing the parts. The sensor mechanism 34 includes a light gate source 36 and a light gate sensor 38 which provides the part sense signals when the light emitted by the light gate source 36 is interrupted by the moving parts 12. Each signal from the light gate sensor 38 is received by the input/output module 24 and thereby communicated to the general purpose computer 22.

Figure 12:
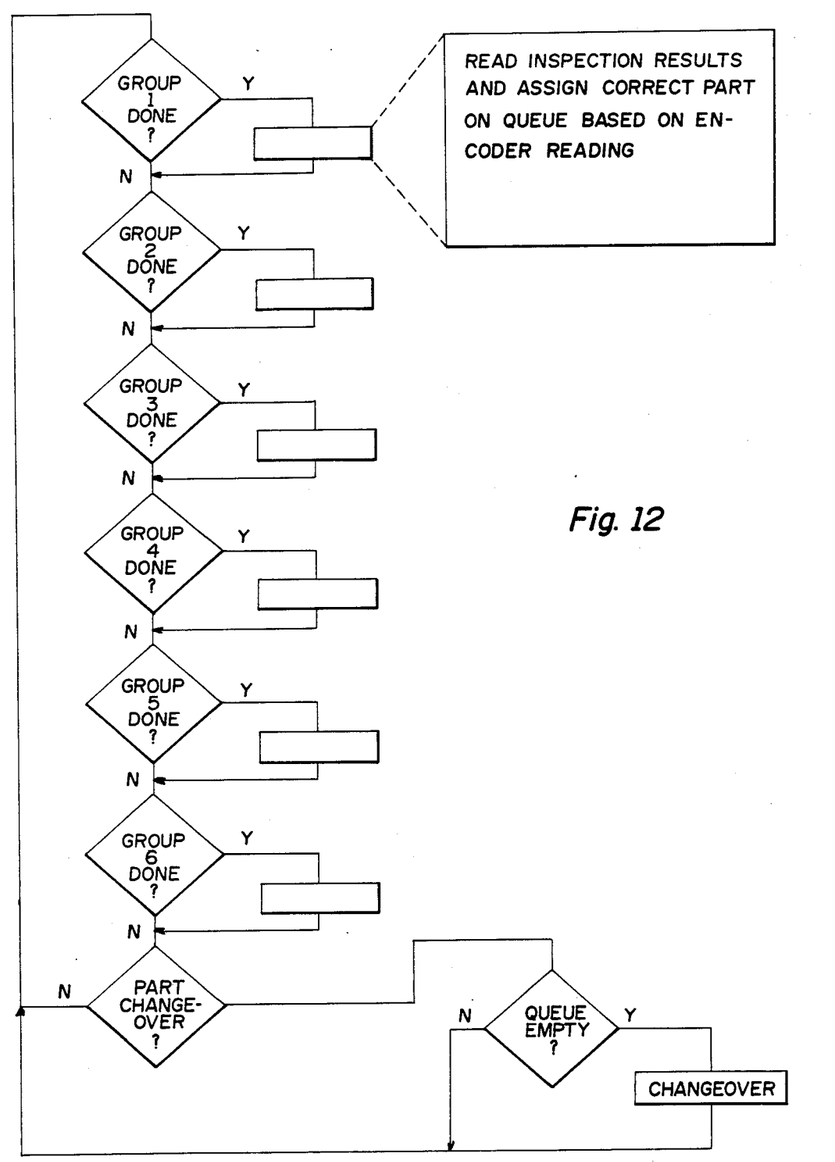
FIG. 12 is a software flowchart of a polling routine which operates in the foreground of the run mode and which operates in an interruptable fashion.

A generating means or mechanism comprising an incremental encoder 40 is coupled to the conveyor 14 and generates a transport signal corresponding to the distance the parts 12 are conveyed by the conveyor 14 in a conventional fashion. The encoder 40 generates quadrature signals which are received by a coordination means or processor 42 which, in turn, translates the quadrature signals to up/down pulses for use by the rest of the machine vision system. The coordination processor 42 includes an encoder counter, the state of which indicates the position of the conveyor 14. A foreground program of the machine vision system, which is indicated in flowchart fashion in FIG. 12, is interrupted on a regular basis in order to update the counter. Preferably, during the inspection process the position of the conveyor belt is updated every 0.002 seconds.

Figure 13:
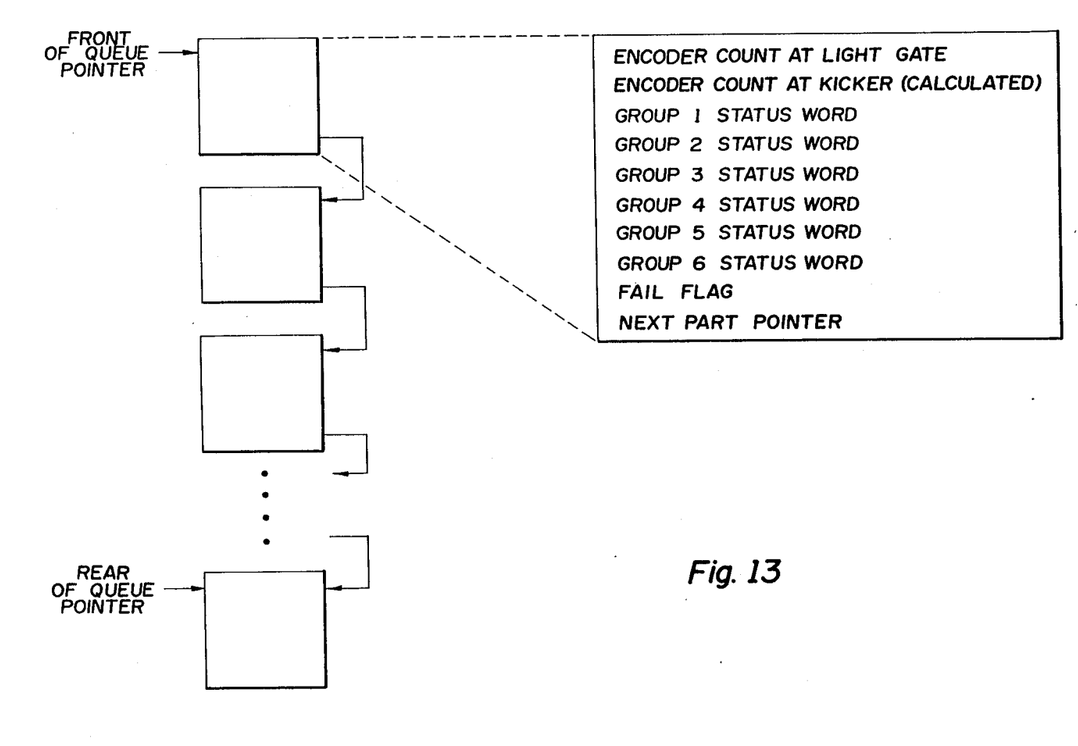
FIG. 13 is a schematic view illustrating the data structure located in memory relating to a queue of parts within the system.

The encoder counter is accessible to the general purpose computer 22 and thereby notes the position of every part which interrupts the light from the light gate source 36. As before, the foreground program of the machine vision system is interrupted whenever a part sense signal is received. The computer 22 notes the count in the counter and a new part record is added to the data structure as illustrated in FIG. 13. The computer 22 then determines the position of the sensed part at which it is to be ejected if it is unacceptable and stores this information as illustrated by the second data entry in FIG. 13. In this way, the parts are tracked by the system 10 as they travel past the light gate source 36 through the vision station 20 and to the reject actuator 26.

The system 10 can be characterized as a model-based inspection system. Before the system 10 is capable of inspecting a stream of parts, the system 10 must first be trained or taught what an "acceptable" part looks like. In general, the system 10 can be taught by showing it a number of ideal or acceptable samples of each of the parts to be inspected. In the preferred embodiment of the invention, the system 10 can learn up to 50 different models of parts.

Figure 4:
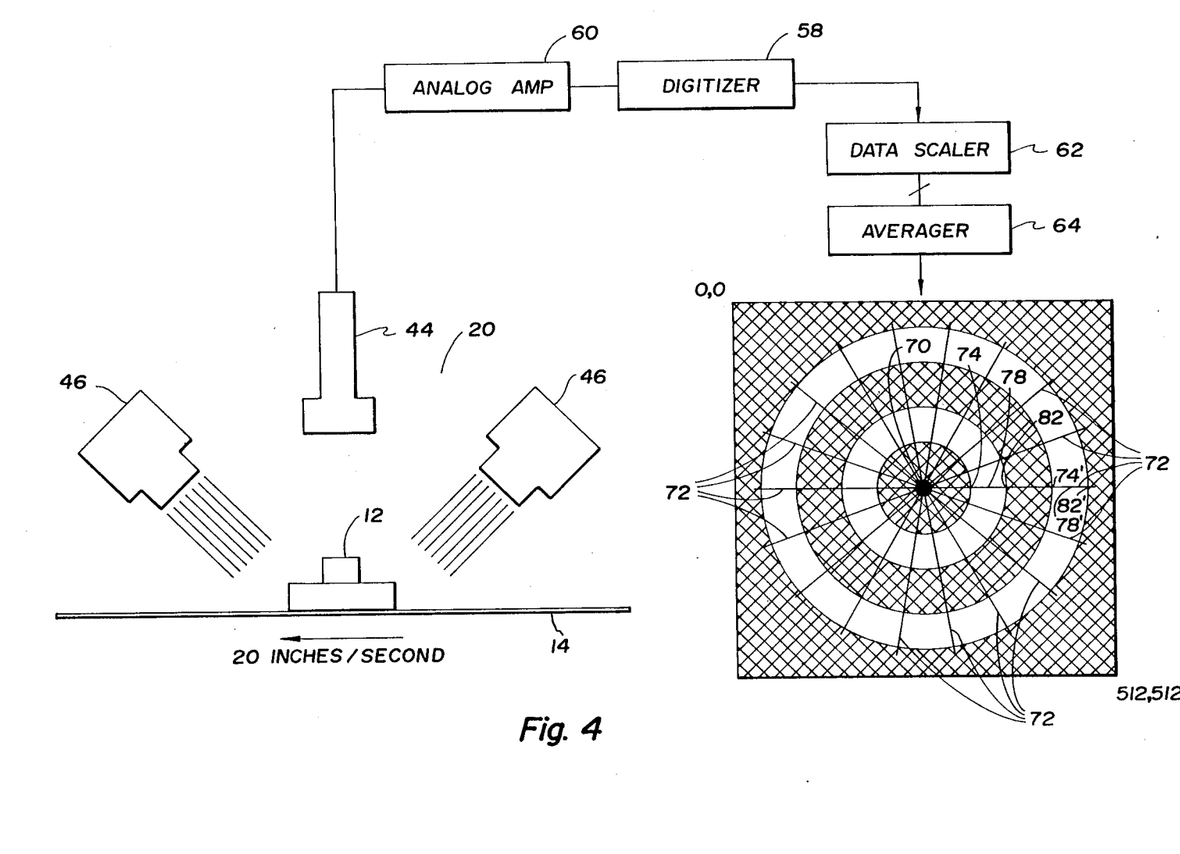
FIG. 4 is a schematic view of the various hardware and software for generating a gray-scale digital image of the part located at a vision station and the resulting gray-scale digital image, including radial scan lines emanating from a centroid of the part.
Figure 11A:
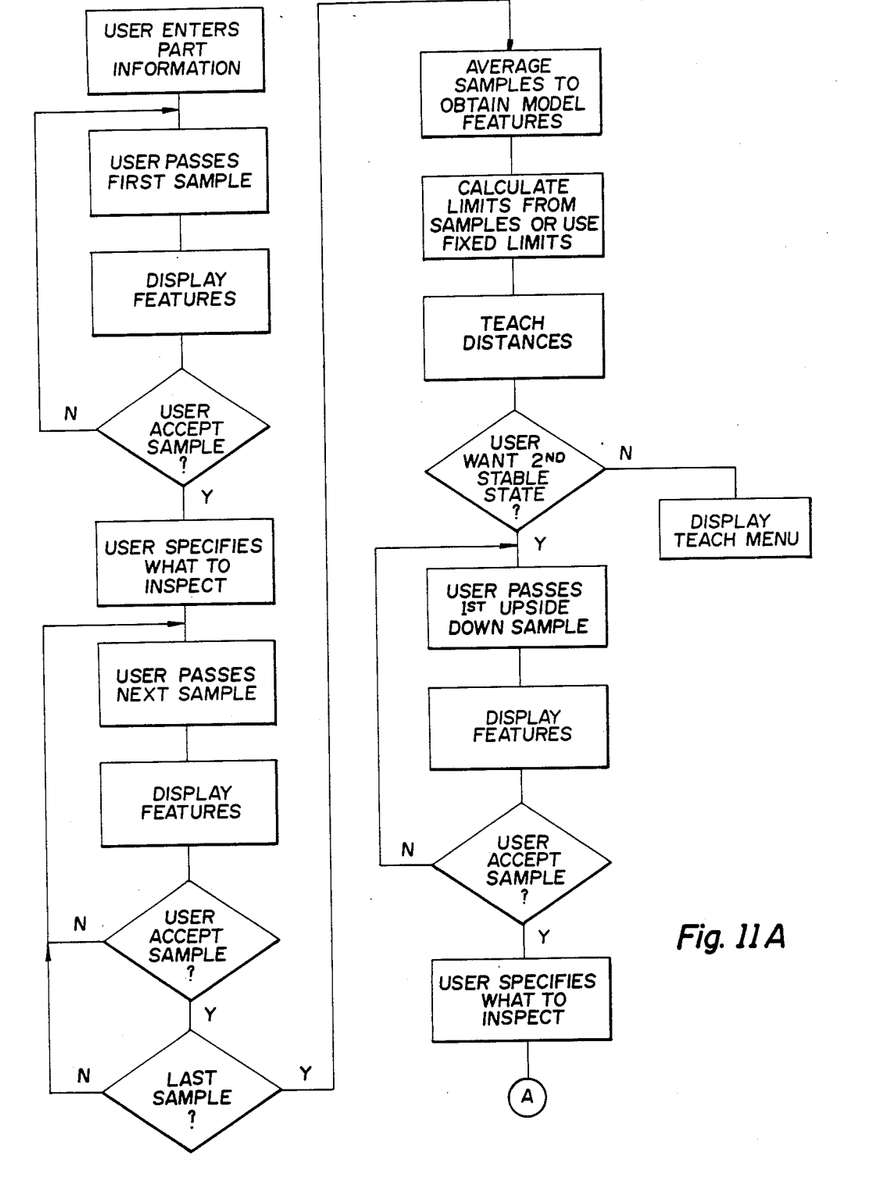
FIGS. 11A and 11B are software flowcharts illustrating the various steps required to create models of parts in a teach mode so that they can be subsequently inspected in a run mode of the system.
Figure 11B:
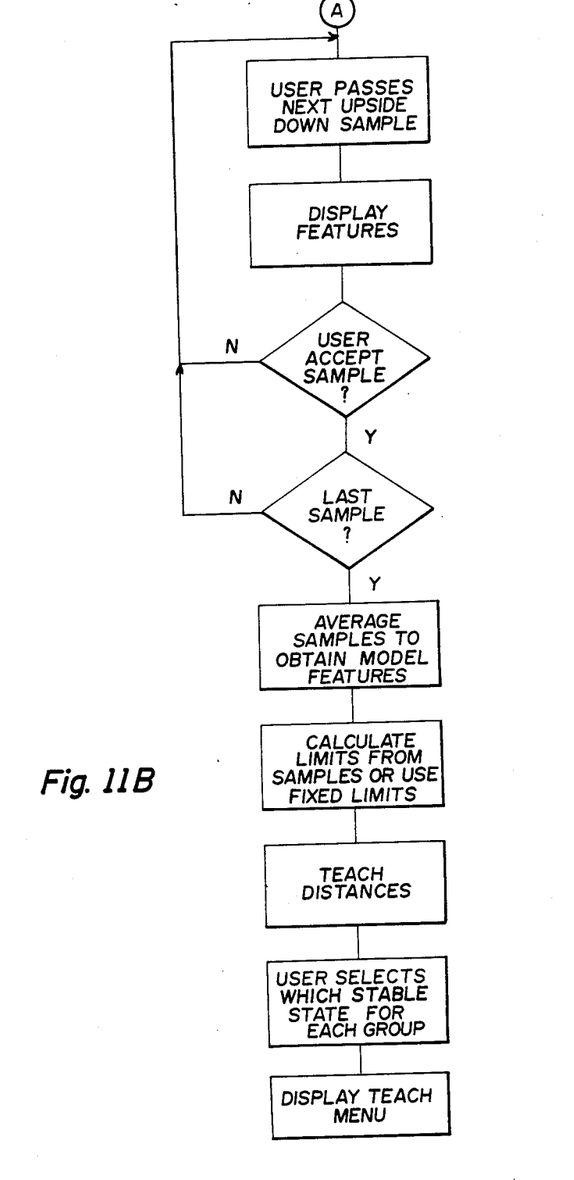

As illustrated in FIGS. 11A and 11B, the user first enters the part number for the parts to be inspected. Then, a first sample of the part is passed through the vision station 20 as shown in FIG. 4 where one or more of the cameras 44 takes a picture of the part 12. Each of the cameras 44 preferably comprises a 2048 element solid state line camera. While only one camera is shown in FIG. 4, it is to be understood that a plurality of such cameras are arranged at the vision station 20 to provide, for example, the top and two side views or scenes of each part to be inspected with the optical setup. Also, preferably, high intensity quartz halogen lamps 46 illuminate each part 12 to provide adequate contrast. While the lamps 46 illustrated in FIG. 4 provide a top view or scene of the part 12, it is to be understood that to obtain adequate contrast for other types of views, such as side views, the scenes may be back lit, lit from the top and/or side lit.

Figure 2:
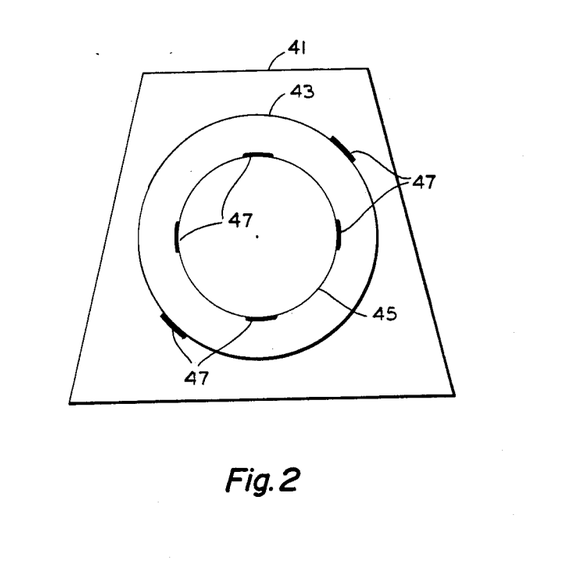
FIG. 2 is a top plan view, illustrating various geometric features of a part to be inspected in bold lines.

Referring again to the software flowchart of FIGS. 11A and 11B, when the first sample part 12 passes in front of the camera 44, all recognizable features such as the part edges 41, 43 and 45 shown in FIG. 2 and their centroids are displayed on a color monitor 48 under control of the computer 22. The color monitor 28 is provided so that each feature is displayed in a different color. Each displayed feature is preferably represented in memory as 1,024 x,y pairs plus its centroid, (Xc,Yc). The features are typically highlighted in red one at a time and the operator may select one or all of them for inspection in the run mode of the system 10. For example, the edge feature 41 may not be inspected while the features 43 and 45 may be inspected. Using interactive graphics through a keyboard 50, the operator may select all 1,024 points of each feature or any subset of the points to be inspected as illustrated by the bold lines 47 of FIG. 2.

Figure 3:
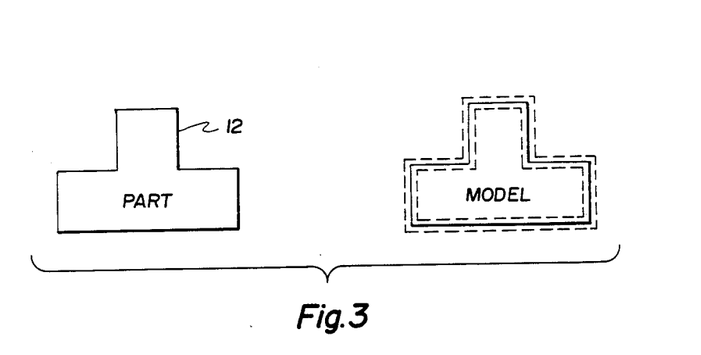
FIG. 3 is a side elevational view of the part and its respective model which illustrates a feature to be inspected and its limits.
Figure 10:
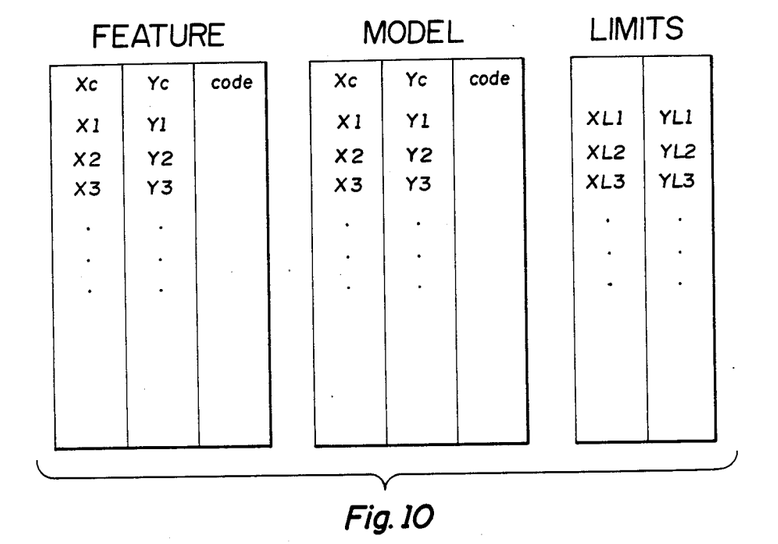
FIG. 10 illustrates feature, model and limit tables corresponding to the part and model of FIG. 3.

Referring also to FIG. 3, subsequent sample parts are then passed in front of the camera 44 and are subjected to a "simulated" inspection. If the sample is "accepted" by the operator, it will be averaged into a final model and if a particular sample is rejected, it will not be averaged into such a model. Model and limit tables are subsequently created for each feature of each scene to be inspected, as shown in FIG. 10. The limit table represents the maximum x and y deviations from "ideal", based upon all accepted samples. The system is also capable of accepting fixed limits for each of the features through the keyboard 50 without the need for passing a number of samples in front of the cameras 44. The operator also enters a conveyor travel distance in terms of a number of encoder pulses to establish a window size in which each processor group must complete its processing for each part in its turn.

As further illustrated in FIGS. 11A and 11B, the parts may be brought in two fixed, stable states, i.e. right side up or upside down, during the training process. Typically, redundant scenes are required, one for each state since oftentimes the parts 12 may be positioned on the conveyor 12 in either of the two states. Thereafter, the model and limit data is then stored in nonvolatile memory, such as a nonvolatile RAM 52, for use thereafter during the actual inspection process. Preferably, the RAM 52 comprises a pair of 40-megabyte Winchester disks.

The coordination processor 42 controls and coordinates different groups of pipelined processors, generally indicated at 54 and 54'. In turn, a first processor or front end vision processor board 56 of each of the groups of processors 54 controls one of four cameras and its respective digitizer 58 and 58'. In this way, each group of processors 54 is capable of selecting one of four cameras located in the vision station 20 and its respective digitizer 58. The number of active groups of processors 54 and 54' is equal to the number of scenes of the particular part 12 which must be processed substantially simultaneously. Each time a known acceptable part is sent to the vision station 20 after the first sample is processed in the teach mode, the processor groups 54 and 54' automatically find the features previously taught as described above. The x,y coordinates of each feature point X1, Y1, etc. and the feature centroid coordinates Xc, Yc appear in a model table as shown in FIG. 10. The table is subsequently stored in the RAM 52.

Figure 6:
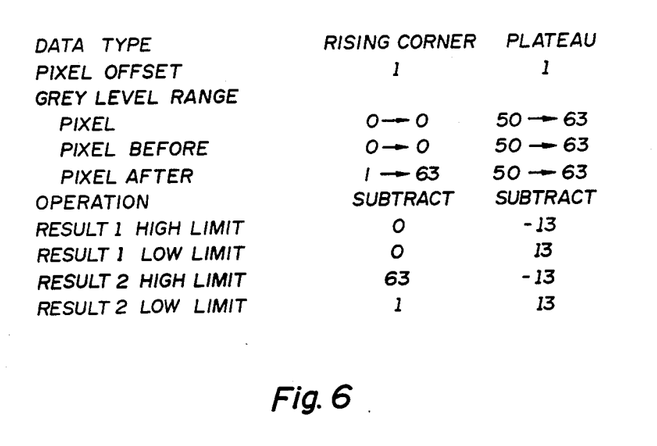
FIG. 6 is a table illustrating two different data types of the radial data and typical algorithms utilized to determine the particular data type.

During the teach mode, the particular camera to be utilized by any particular group of processors 54 is specified as well as the type of picture to be analyzed (i.e. front lit versus back lit). Also, various parameters are loaded during the teach process including picture size. In order to detect a point in a particular feature during the teach mode, the characteristics of the particular feature are taught, such as data type (i.e. positive slope, negative slope, corners, peaks, etc.) gray level range for each data type, the operator used to determine the data type, [usually $(A-B)$ or $k(A-B)/(A+B)$ where A and B are gray level values] number of data types in succession that must be used, the weight of each data type and the binary code for each final data type. Such data is illustrated in FIG. 6 for a rising corner and plateau data types. In this way, lookup tables of data type detecting algorithms are created which are also stored in the RAM 52.

Referring again to FIG. 4, prior to being digitized by the digitizer 58 a television output signal containing a sample part or a part to be inspected is first amplified by an analog amplifier 60. The subsequently digitized signal is then scaled by a data scaler 62 on the front end board 56 so that the data has a gray level between 0 to 63. The data is then averaged by a data averager 64. The averaging process takes place in order to compress the data from a 2,048 by 2,048 block of data into a 512 by 512 block of data and to provide noise filtering. The 512 by 512 block of data is received from the first processor 56 by a second processor or picture memory processor board 66 via a video bus 68. The second processor 66 receives encoder pulses from the coordination processor 42 to thereby store the 512 lines synchronously with the encoder pulses. In particular, as the beginning of a new part is sensed. The second processor 66 stores "m" lines of digitized video where each line represents the "n"th line of data provided to it by the first processor 56. The second processor 66 continuously senses the occurrence of every "n"th line by monitoring a status signal appearing on a line 69.

Figure 5:
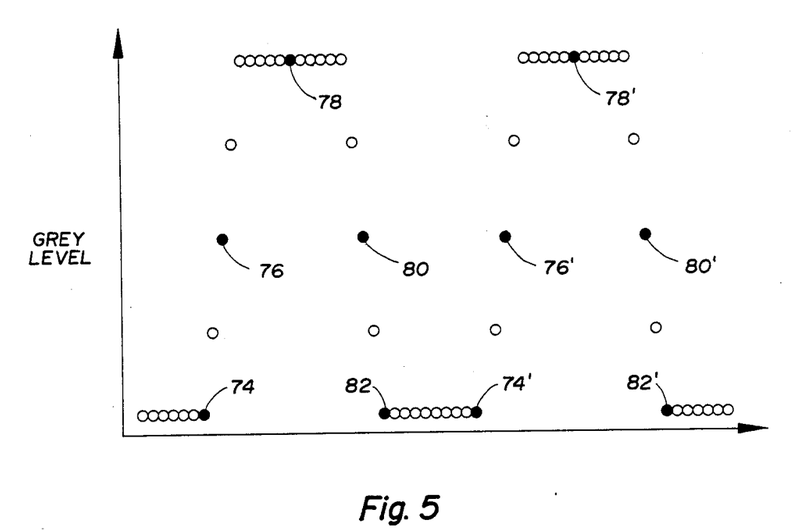
FIG. 5 is a graph illustrating the gray level of pixels along one of the radial scan lines illustrated in FIG. 4.

While storing the gray-scale digital image the second processor 66 calculates the centroid 70 of the part currently in view. The second processor 66 then scans the gray-scale digital image as illustrated in FIG. 4 in a radial fashion along ray lines 72. The resulting pixel values along one ray line are illustrated in FIG. 5. A pixel 74 indicates a first rising corner, a pixel 76 indicates a first rising slope, a pixel 78 indicates a first plateau, a pixel 80 represents a first falling slope and a pixel 82 represents a falling corner. The same numerals having a prime designation indicate a second set of such pixels along the same ray line.

Each radial data point consists of a picture point shade (or gray level) value of 0 to 63 and its corresponding x,y coordinates within the picture. A radial line consists of a series of these points. A radial picture consists of a series of radial lines usually covering 360 degrees as indicated in FIG. 4. Typically 1024 radial lines are scanned thereby detecting 1024 points for each feature.

The radial data is sent on a data bus 84 by the second processor 66 to the first processor 56 and the corresponding x,y coordinates of the radial data is sent along a bus 86. In general, the first processor 66 reads the radial data points in a serial fashion from the second processor 66 and detects data type codes and their corresponding x,y coordinates.

In general, data type codes represent the characteristics that are desired to be recognized in each radial data line of any given scene. Typical data type codes represent positive and negative slopes, high and low negative corners, peaks, valleys, average characteristics, etc. During the teach mode, the rules or algorithms for finding the particular data types for a given scene are provided. For example, as indicated in FIG. 6, in order to find a rising corner point, such as corner points 74 or 74', pixels before and after a particular pixel under test must be looked at. The pixel offset of one requires that the pixels one position away from the test pixel shall be the "pixel before" and the "pixel after". The ranges 0 to 0 require that the indicated pixels have a gray level of 0. The "pixel after" shall have a level from 1 to 63. Pixel comparisons shall be made by subtracting the test pixel value from the others. Testing against the "pixel before" shall yield a remainder of 0 and testing against the "pixel after" shall yield a remainder between 1 and 63. If all these conditions are met the test pixel is a rising corner data type. The plateau algorithm requires that the three pixels all have a gray level value of 50 to 63 and in each case subtraction shall yield a remainder between −13 and 13. An inspection of FIG. 5 shows that the pixels 78 and 78' will qualify as plateau data types but several neighboring pixels will also meet the test. To resolve any ambiguity, there is another rule, not shown in FIG. 6, that if consecutive pixels are of the same data type the average position is chosen as the data type point.

Figure 7:
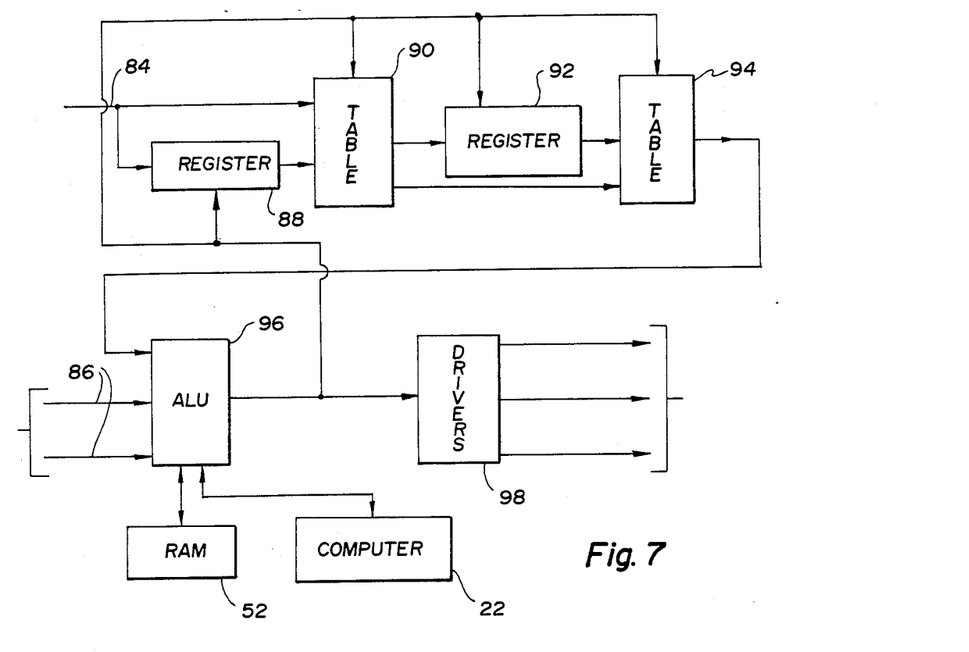
FIG. 7 is a schematic view illustrating the hardware of the present invention utilized to convert the radial data into data type codes.

Referring to FIG. 7, there is indicated the hardware utilized to convert those radial data points representing data types into a stream of data type codes and their corresponding x,y coordinates. The algorithms like those illustrated in FIG. 6 are effectively embodied in two lookup tables acting serially on the three pixels of interest to determine the fit of the pixels to the data type criteria. All the algorithms for the image being processed are incorporated into these two tables. A programmable delay or multi-stage shift register 88 allows selected pixels in the stream of pixels to be algebraically combined. A lookup table 90 is programmed with the algorithm type and the pixel range from the computer 22 through an arithmetic logic unit or ALU 96 to obtain a first level data type code. The first level data type code is then fed into a second programmable delay or multi-stage shift register 92 with data from the computer 22 indicating what data types at the first level are to be considered by the particular algorithm. The outputs of the programmable delay 92 and the table 90 are input into a second lookup table 94 which finally determines the data types.

The computer 22 and its RAM 52 are coupled to the ALU 96 to, in turn, load the previously taught information, including algorithm type and pixel range, into the first and second lookup tables 90 and 94 and the delay 92 before the parts 12 are inspected. The ALU 96 then combines the data type codes with the respective coordinate information appearing on lines 86 and the resulting data type codes and their x,y coordinates are sent to drivers 98 to provide the data type codes and coordinate information to a third processor or segmentation and inspection processor board 100.

Figure 8:
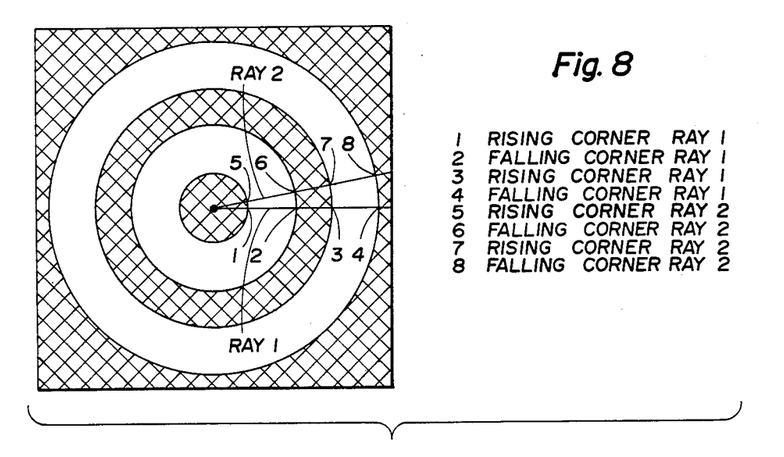
FIG. 8 is a graphic illustration of the radial data and the data type codes assigned to the radial data.
Figure 9:
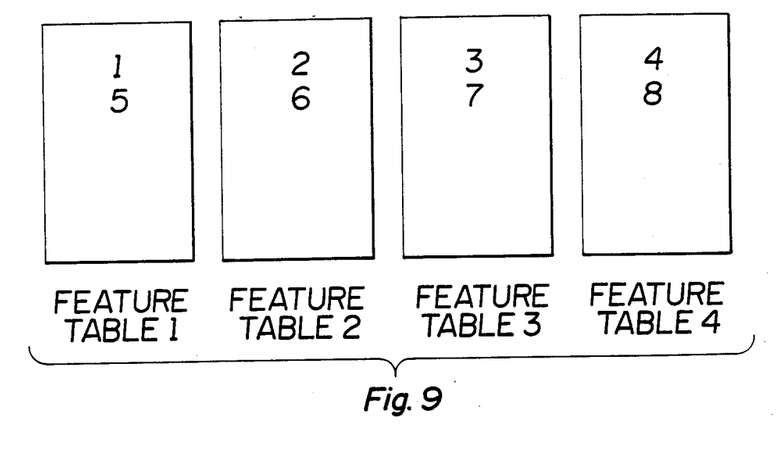
FIG. 9 illustrates steps taken in forming feature tables of the data type codes of FIG. 8.

In general, the segmentation and inspection board 100 organizes the data type points into feature tables wherein all of the points in a particular table have the same code and consecutive points in the table are relatively close to each other. Thus the segmentation algorithm tests for data type code and for proximity to a previous point in the table. The segmentation and inspection processor board 100 reads the data type codes and their coordinates which appear on lines 102 and 104, respectively. The data is then processed into feature tables as shown in FIG. 9 according to the illustration of FIG. 8 to build a data base which forms the basis for inspecting the part 12. For example, with respect to FIG. 8, points 1 and 5 both relate to the same data type code of a rising corner but of different adjacent rays. They are in close proximity and thus are assigned to the same table. Points 1 and 3 (or 1 and 7), on the other hand, are of the same data type but are not in close proximity so they belong in different feature tables. When the particular feature within feature table 1 is complete as illustrated by the feature table in FIG. 10, the feature in the table will represent an entire circle. Preferably, data for each feature is placed in a table housing 1024 x and y coordinates. Thus the data type detection algorithm of FIG. 6 and the segmentation algorithm together comprise a feature detecting algorithm.

After the segmentation and inspection board 100 has completed all its feature tables, the first and second processor boards 56 and 66, respectively begin to process the next part as it enters its camera's field of view. Part spacing is limited by the combined and overlapping processing time to create the radial data, the data type code data and the data base of feature tables.

Figure 14:
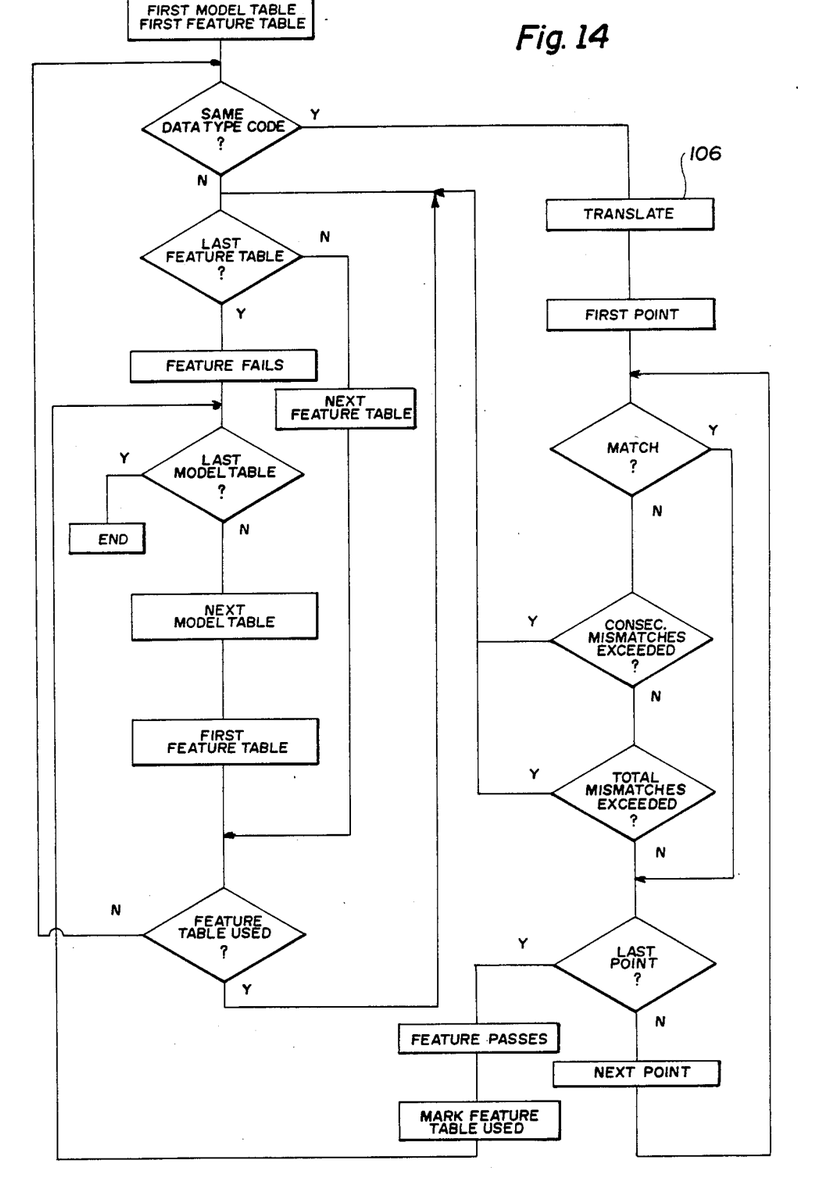
FIG. 14 is a flowchart of an inspection routine utilizing the various feature, model and limit tables, such as illustrated in FIG. 10.

The segmentation and inspection board 100 preferably itself compares the feature tables with the model and limit tables as illustrated by the algorithm of FIG. 14. In order to compare the model table with each of the feature tables having the same type code, the features must be translated as illustrated by block 106 so the point by point inspection can be performed. The system 10 fails features based on the total number of mismatches allowed per feature and/or the number of consecutive mismatches per feature. The system rejects parts based on failed features or lack of concentricity.

The results from each of the segmentation and inspection boards 100 are then passed to the general purpose computer 22 which then determines the overall inspection result of the part as illustrated by FIG. 12 which indicates the use of groups of processors to inspect a part. If the part is determined to be "acceptable" by the general purpose computer 22, the part proceeds down the conveyor 14 into its shipping container 30. If the part is rejected the computer 22 has already determined from the quadrature signals received through the coordination processor 42 and from the data as indicated in FIG. 13 when the part is in front of the reject actuator 26 at which time the part is kicked off into the unacceptable part or reject container 28.

When a different type of part is to be inspected, a part code is entered by the operator and thereafter the part changeover for the system 10 is totally automatic. As further illustrated by FIG. 12, after processing all of the old parts in its queue, the system 10 automatically activates a new pattern of lights and cameras under control of the first processor boards 56 of the groups of pipeline processors 54. Model data and the parameters of the new parts are downloaded from the RAM 52 of the computer 22 into each of the processor boards 56, 66 and 100.

The above-noted method and system is capable of inspecting a wide variety of parts at a vision station having a single optical setup. Part inspection information can thereafter be communicated to any type of peripheral device. The system tolerates noisy, relatively low contrast images and is easily taught.

The invention has been described in an illustrative manner and it is to be understood that the terminology which has been used is intended to be in the nature of words of description rather than of limitation.

Obviously, many modifications and variations of the present invention are possible in light of the above teachings.

The embodiments of the invention in which an exclusive property or privilege is claimed are defined as follows:

1. A method of automatically inspecting a part at a vision station, the method comprising the steps of:
   generating a gray-scale digital image of the part to be inspected;
   detecting feature points corresponding to at least one feature of the part by scanning along a pattern of lines in the image, each line comprising a series of gray-scale pixels, and comparing sequences of pixels in the line to criteria for each feature of interest to determine feature point coordinates;
   storing sets of detected feature point coordinates in separate tables for each feature; and
   comparing each set of feature points to a predetermined reference set of feature points to determine whether the part is acceptable.

2. A method of automatically inspecting a part at a vision station, the method comprising the steps of:
   generating a gray-scale digital image of the part to be inspected;
   determining the centroid of the part image;
   detecting feature points corresponding to at least one feature of the part by scanning along a pattern of radial lines in the image emanating from the centroid, each line comprising a series of gray-scale pixels, and comparing sequences of pixels in the line to criteria for each feature of interest to determine feature point coordinates;
   storing sets of detected feature point coordinates in separate tables for each feature; and
   comparing each set of feature points to a predetermined reference set of feature points to determine whether the part is acceptable.

3. A method of automatically inspecting a part at a vision station, the method comprising the steps of:
   (a) generating a gray-scale digital image of a model part;
   (b) determining the centroid of the part image;
   (c) scanning along a pattern of radial lines in the image emanating from the centroid and detecting feature points in the lines corresponding to at least one feature of the part;
   (d) storing sets of feature point coordinates in separate tables for each feature;
   (e) generating a gray-scale digital image of the part being inspected;

(f) repeating step (b) through (d) for a part being inspected; and (g) comparing each set of feature points for the part being inspected to a corresponding set of model feature points to determine whether the part is acceptable.

4. A method of automatically inspecting a part at a vision station, the method comprising the steps of:
   generating a gray-scale digital image of the part being inspected, the part having at least one feature;
   defining for each feature a data type algorithm and a set of reference data comprising feature data points of an ideal feature;
   performing each algorithm on at least a portion of the gray-scale digital image of the part to generate a set of data type points;
   segmenting the data type points into discrete features by assigning each data point to a set of identical data type and in close proximity to other such points;
   storing sets of segmented feature point coordinates in separate tables for each feature; and
   comparing each set of feature points to the reference set of ideal feature points to determine whether the part is acceptable.

5. A method of automatically inspecting one of at least two different parts at a vision station, each part having at least one feature, the method comprising the steps of:
   generating a gray-scale digital image of the part to be inspected;
   defining for each part and for each feature a data type algorithm and a set of reference data comprising feature data points of ideal parts;
   storing the algorithms and the reference data;
   retrieving the algorithms and the reference data for the one of the two parts being inspected;
   performing each retrieved algorithm on at least a portion of the gray-scale digital image of the part to generate a set of data type points;
   segmenting the data type points into discrete features by assigning each data point to a set of identical data type and in close proximity to other such points;
   storing sets of segmented feature point coordinates in separate tables for each feature; and
   comparing each set of feature points to the retrieved reference set of ideal feature points to determine whether the part is acceptable.

6. A gray-scale vision system for automatically inspecting a part at a vision station, the system comprising:
   means for generating a gray-scale digital image containing the part to be located at the vision station;
   means for storing tables containing feature reference data relating to at least one feature of an ideal part a predetermined data type detecting algorithm for each type of feature to locate data type sets within the digital image and limit data relating to the allowable deviation of the feature;
   means for performing the algorithm with at least a portion of the digital image to provide data type sets;
   means for sorting the data type sets into separate features and storing the feature data in separate tables, and
   means for comparing the located feature data with the reference data to determine whether the part is acceptable.

7. A system for automatically inspecting a plurality of substantially identical parts, the system comprising:
   a conveyor for conveying the parts from an upstream position to a downstream position;
   generating means coupled to the conveyor for generating a transport signal corresponding to the distance that the parts are conveyed along the path of conveyance on the conveyor;
   sensor means located along the path of conveyance for sensing the parts as the parts are conveyed by the conveyor past the sensor means and providing part sense signals upon sensing the parts;
   means for generating gray-scale digital images containing different views of each of the parts at a vision station, said means for generating including at least one camera for each view;
   means for storing tables containing feature reference data relating to at least one feature of an ideal part a predetermined data type detecting algorithm for each type of feature to locate data type sets within the digital image and limit data relating to the allowable deviation of the feature;
   means for performing the algorithm with at least a portion of the digital image to provide data type sets;
   means for sorting the data type sets into separate features and storing the feature data in separate tables;
   means for comparing the located feature data with the reference data to determine whether each of the located features is acceptable and to provide feature-acceptance signals; and
   processing means for processing the transport signal, the part sense signals and said feature-acceptance signals to provide reject signals for use by an actuator to remove unacceptable parts from the path of conveyance.

8. A gray-scale vision system for automatically inspecting one of at least two different kinds of parts at a vision station, the system comprising:
   means for generating a gray-scale digital image containing the part to be inspected at the vision station, said means for generating including at least one television camera;
   means for storing tables containing feature reference data relating to at least one feature for each of first and second ideal parts, data type detecting algorithms for each type of feature to locate the data type sets of the two different kinds of parts within the digital image and limit data relating to the allowable deviation of each of the features;
   means for retrieving the tables relating to one of the two different parts to be inspected at the vision station;
   means for performing each retrieved algorithm with at least a portion of the digital image to provide data type sets;
   means for sorting the data type sets into separate features and storing the feature data in separate tables;
   means for comparing the located feature data with the corresponding retrieved feature reference data to determine whether the part is acceptable.

9. A system for automatically inspecting a part at a vision station, the system comprising:

means for generating first and second gray-scale digital images containing first and second views of the part to be inspected at the vision station, said means for generating including at least two television cameras;

means for storing tables containing feature reference data defining first and second features of an ideal object, first and second feature-detecting algorithms to locate their respective features within their respective digital images and first and second sets of limit data relating to the allowable deviation of their respective features;

means for performing the first feature-detecting algorithm with at least a portion of the first digital image to provide a first set of located feature data;

means for performing the second feature-detecting algorithm with at least a portion of the second digital image to provide a second set of located feature data;

means for comparing the first set of located feature data with the first set of reference data and limit data to obtain a first feature-acceptance signal;

means for comparing the second set of located feature data with the second set of reference data and limit data to obtain a second feature-acceptance signal; and processing means for processing said first and second feature-acceptance signals to determine whether the part is acceptable.

10. A gray-scale vision system for automatically inspecting a plurality of first and second kinds of parts, the system comprising:

generating means including at least two cameras located at a vision station, a digitizer coupled to each of the cameras for digitizing the output signals of the cameras to provide gray-scale digital data, said generating means generating gray-scale digital images of at least two views of each of the parts at the vision station and a corresponding illumination subsystem for each of the cameras, each of the cameras providing a different view of the part being inspected;

a conveyor for continuously conveying the parts from an upstream position to a downstream position, said vision station being located along the path of conveyance;

encoder means coupled to the conveyor for generating a transport signal corresponding to the distance the parts are conveyed along the path of conveyance on the conveyor;

sensor means located along the path of conveyance for sensing the parts as the parts are conveyed by the conveyor past the sensor means and providing part sense signals upon sensing the parts;

means for storing tables of feature reference data defining at least one feature for each of the views of first and second ideal parts of their respective first and second kinds of parts, said tables including data type detecting algorithms to locate the data types in the digital images and limit data relating to the allowable deviation of the features for each of the first and second types of parts;

at least two groups of programmed processors, each of said groups of processors including a plurality of pipelined processors coupled to operate in serial fashion on the gray-scale digital data for one of said views, a first programmed processor in each of said groups of processors controlling a selected one of said cameras and its respective digitizer for acquiring the gray-scale digital data;

a second programmed processor in each of said groups of processors storing the gray-scale digital image containing one of the views of the part to be inspected and radially scanning the image to provide radial data, said first processor performing a feature-detecting algorithm with the radial data to provide feature-coded data;

a third programmed processor in each of said groups of processors segmenting the feature-coded data to obtain located feature data and comparing the located feature data with the model data for its respective feature to determine whether the located feature is acceptable and to provide a feature-acceptance signal;

coordination means coupled to each of said group of processors and responsive to said transport signal to coordinate the operation of each of said group of processors;

a central processor coupled to said coordination means and responsive to said feature-acceptance signals and the part sense signals to provide reject signals for use by an actuator to remove unacceptable parts from the path of conveyance wherein said groups of processors operate substantially simultaneously; and means coupled to said means for storing for programming each of said groups of processors with its respective reference data.

11. The system as claimed in claim 6 or claim 7 or claim 8 or claim 9 or claim 10 wherein the located feature data comprises a plurality of discrete points and wherein the system includes means for individually comparing the discrete points to a corresponding part of the model data.

* * * * *